United States Patent
Harder et al.

(10) Patent No.: US 6,423,066 B1
(45) Date of Patent: *Jul. 23, 2002

(54) NECK SCREW

(75) Inventors: Hans Erich Harder, Probsteierhagen; Bernhard Karich, Ot Purschwitz, both of (DE)

(73) Assignee: Stryker Trauma GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 12 days.

(21) Appl. No.: 09/468,655

(22) Filed: Dec. 21, 1999

(30) Foreign Application Priority Data

Dec. 28, 1998 (DE) .......... 298 23 113

(51) Int. Cl.[7] .............................. A61B 17/74
(52) U.S. Cl. .............................. 606/65; 606/67
(58) Field of Search .................. 606/60, 62, 64, 606/65, 67, 72, 73

(56) References Cited

U.S. PATENT DOCUMENTS

| | | | |
|---|---|---|---|
| 3,996,931 A | | 12/1976 | Callender, Jr. |
| 4,457,301 A | * | 7/1984 | Walker .................. 606/62 |
| 5,112,333 A | | 5/1992 | Fixel |
| 5,176,681 A | | 1/1993 | Lawes et al. ............ 606/64 |
| 5,352,229 A | * | 10/1994 | Goble et al. ............ 606/72 |
| 3,892,233 A | * | 7/1995 | Vestby ................... 606/67 |
| 5,454,813 A | | 10/1995 | Lawes ................... 606/62 |
| 5,489,210 A | * | 2/1996 | Hanosh ................. 433/173 |
| 5,601,558 A | * | 2/1997 | Torrie et al. ............ 606/72 |
| 5,643,320 A | * | 7/1997 | Lower et al. ........... 606/232 |
| 5,769,852 A | * | 6/1998 | Branemark ............. 606/65 |
| 5,782,919 A | * | 7/1998 | Zdeblick et al. ......... 623/17 |
| 5,827,287 A | * | 10/1998 | Tunc ..................... 606/76 |
| 5,993,450 A | * | 11/1999 | Worcel .................. 606/73 |
| 6,007,539 A | * | 12/1999 | Kirsch et al. ........... 606/75 |
| 6,015,937 A | * | 1/2000 | Branemark ............. 623/16 |
| 6,019,760 A | * | 2/2000 | Vestby ................... 606/67 |

FOREIGN PATENT DOCUMENTS

| | | | | |
|---|---|---|---|---|
| DE | 3509417 | * | 9/1986 | .......... 606/60 |
| DE | 4143362 | * | 1/1993 | .......... 606/60 |
| EP | 0 257 118 | | 3/1988 | |
| EP | 0230856 | * | 1/1993 | .......... 606/60 |
| EP | 0 551 588 | | 7/1993 | |
| EP | 1 016 382 | | 9/2001 | |
| GB | 2 209 947 | | 6/1989 | |

* cited by examiner

*Primary Examiner*—Jeffrey A. Smith
*Assistant Examiner*—Michael B. Priddy
(74) *Attorney, Agent, or Firm*—Lerner, David, Littenberg, Krumholz & Mentlik, LLP

(57) ABSTRACT

A hip neck screw having a shank, a male-threaded portion at the proximal end thereof and areas for engagement by a tool wherein the screw is designed in such a way that it is adapted to be passed through a bore of a supporting device adapted to be mounted on the femur, preferably a locking nail and to be held therein. The neck screw has axially parallel grooves extending from the distal end are formed at opposite sides, of which at least one extends into the threaded portion. A fork-like blade is provided having blade legs which are accommodated by the grooves and has a connecting portion of the legs adapted to be connected to the distal end of the screw shank.

21 Claims, 2 Drawing Sheets

NECK SCREW

BACKGROUND OF THE INVENTION

1. Field of the Invention

This invention relates to a neck screw for an intramedullary nail.

2. Description of Prior Art

U.S. Pat. Nos. 5,176,681 and 5,454,813, the teachings of which are incorporated herein by reference, and also EP 0 257 118, have made known an osteosynthesis aid which consists of a locking nail and a neck screw. The locking nail is driven into the femur from the proximal end. In the proximal portion, the locking nail has an inclined bore the axis of which is directed approximately to the axis of the collum femoris. A neck screw is passed through this bore. It has a threaded portion which is self-tapping for example, and is propelled up into the head of the femur. From the proximal end of the nail, a fixing or set screw is inserted into a bore of the locking nail which, with its inner end, interacts with circumferentially spaced, axially parallel grooves in the shank of the neck screw to secure the neck screw against rotation while allowing it to slide in an axial direction. Such an osteosynthesis aid preponderantly serves for taking care of trochanteral and subtrochanteral fractures, but also for taking care of fractures of the collum femoris or fractures in the head region.

Also, compression may be exercised by means of a compression screw which is screwed into the distal portion of the neck screw and which interacts with the locking nail. This application case occurs where there are fractures in the head and neck areas.

In order that the locking nail and the neck screw may be mounted a target instrument kit is required to locate the bores in the locking nail from outside. Most of them include an instrument which is placed at the proximal end of the locking nail, and which has a strap which extends in a spaced relationship parallel to the femur when connected to the locking nail.

When the osteosynthesis aid described is used complications may occur in the area of the neck screw in taking care of pertrochanteral femur fractures having short head-and-neck fragments or in case of significant osteoporosis. The neck screw may break out when the bone substance is reduced or there is a femoral head malposition. In addition, there is a risk of secondary rotation of the head-and-neck fragment when the neck screw is in an eccentric position. Further, it is known to use a blade in lieu of a neck screw, which is passed through an opening in the locking nail. See for example, U.S. Pat. No. 3,433,220. Such a blade is more favorable with respect to anti-rotational stability. However, inserting the blade is far more problematic. Moreover, the compression of the fracture cannot be achieved by means of a blade.

SUMMARY OF THE INVENTION

It is an object of the invention to create a neck screw wherein the surface subjected to load is enlarged in the threaded portion of the neck screw.

The inventive neck screw has axially parallel grooves formed on opposite outer sides extending from the distal end, out of which at least one extends into the threaded portion. Furthermore, a fork-like blade is provided the legs of which are accommodated by the grooves. The cross-section of the blade legs preferably corresponds to that of the grooves, a slight clearance being left in between, however. The blade legs are interconnected at the distal end via an appropriate connecting portion which, in turn, is connected to the distal end of the neck screw in an appropriate way. Preferably, the connecting portion is annularly cylindrical and its outer diameter is approximately equal to the outer diameter of the shank of the neck screw. It may be attached by means of a screw which is threaded into a female thread at the distal end of the neck screw. Preferably, the annularly cylindrical portion, in turn, has a female thread for connection to an appropriate drive-in instrument.

At least one femur neck blade/groove extends into the threaded portion of the neck screw or even slightly beyond same. Preferably, however, two blade legs are used each approximately equal in length such that both of them will enlarge the surface area subjected to load in the threaded portion of the neck screw. This results in an efficient safety against any secondary head-and-neck rotation. The inventive neck screw is particularly advantageous when used in significant osteoporosis or an eccentric position of a coxa screw.

The grooves or blade legs are preferably designed in such a way that the outer surfaces of blade legs are position approximately at the level of the shank outer surface in the shank area of the neck screw. In another aspect of the invention, the grooves are adapted to extend in a more planar way or have a more shallow depth in the area of the threaded portion, a ramp being adapted to be provided between the groove sections which are different in depth. As a result, the blade legs will be spread apart and, hence, will be anchored more efficiently.

In another aspect of the invention, the ends of blade legs have a chamfer at their outside. This makes it easier to drive them in. In another aspect of the invention, the ends of blade legs are chamfered at their inside, which makes it easier to insert them in the grooves. This aim is also served by option chamfers in the groove walls in the entry area of blades as well as at the bottom of the groove.

The inventive neck screw is implanted in a usual manner. After being screwed in, it is fixed in the sense of rotation as is the case for the osteosynthesis aid described in the beginning, using a fixing screw and axially parallel grooves, for example, at the outside of the screw shank. A compression of the fracture may be effect if needed. Afterwards, the blade will be driven in, which may be watched via an image converter. When the blade legs should extend in a way that they protrude beyond the proximal end of the neck screw this may be seen on the image converter. After the driving member is removed the blade may be secured against any slide-out by means of a screw which is turned into the above-described female thread at the proximal end of the neck screw.

The inventive neck screw is fully compatible with the conventional, above-described osteosynthesis aid. The conventional target instrument kit may be used. The dynamic way of supporting the neck screw may be maintained. It is easy to handle the inventive neck screw. Explanation does not pose problems either. As an alternative, however, the inventive neck screw may even be inserted without an arresting blade.

The sole difference that proves to exist as compared to the conventional neck screws which are described above is that only two sliding and fixing grooves can be formed in the screw shank because blade-receiving grooves are out of question for the purpose here.

BRIEF DESCRIPTION OF THE DRAWINGS

The invention is now explained in detail below by way of an embodiment illustrated in the drawings.

DESCRIPTION OF THE PREFERRED EMBODIMENTS

Figure 1:
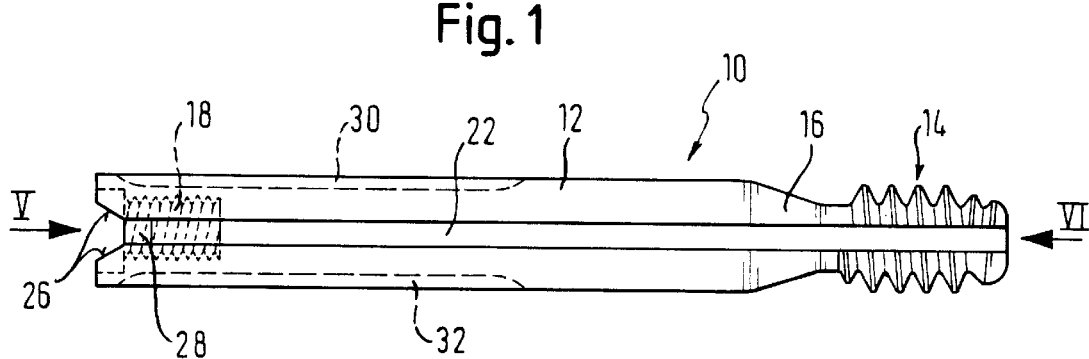
FIG. 1 shows a diagrammatical side view of a neck screw according to the invention.

A neck screw 10 of FIG. 1 has a cylindrical shank 12 and a threaded portion 14 wherein shank 12 opens into the threaded portion 14 via a tapered portion 16. The major diameter of the self-tapping thread of threaded portion 14 approximately corresponds to the outer diameter of shank 12. The threaded portion 14 proceeds to end in the proximal end of screw 10. At the distal end, shank 12 has a female-threaded portion 18 which continues to end in a through bore or cannulation 20. The through bore serves to accommodate a pointed guide wire or bar used in implanting the neck screw.

Figure 5:
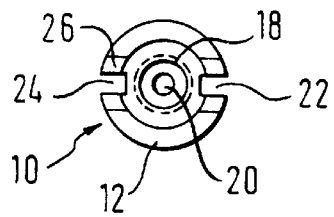
FIG. 5 shows the end view of the screw of FIG. 1 in the direction of arrow 5.
Figure 6:
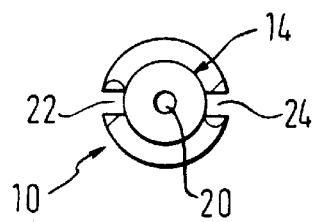
FIG. 6 shows the end view of the screw of FIG. 1 in the direction of arrow 6.
Figure 7:
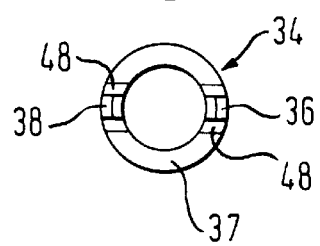
FIG. 7 shows the end view of the screw of FIG. 3 in the direction of arrow 7.
Figure 8:
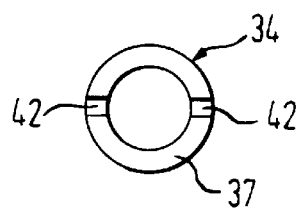
FIG. 8 shows the end view of the screw of FIG. 3 in the direction of arrow 8.

At least one groove 22 extending to the proximal end of shank 12 is provided. In the preferred embodiment, on a diametrically opposed sides, grooves 22, 24 extend across the length of nail 10 wherein only one groove 22 can be seen in FIG. 1 whereas also a groove 24 can be seen in FIGS. 5 and 6. The grooves are of an approximately square cross-section. The groove wall expands to the distal end in a chamfer as can be seen at 26 in FIG. 1. The groove bottom has a chamfer 28, i.e. the groove 22, 24 initially is deeper than it is in the remaining area when viewed from the distal end. For the rest, grooves 22, 24 may be slightly smaller in depth in the area of threaded portion 14. This, however, is not illustrated here.

On diametrically opposed sides, slide grooves 30, 32 are formed in 24 in the rear or distal area of the shank 12 and, hence, are offset by 90° each with respect to the grooves 22. They are shown in dotted lines in FIG. 1. Their function will be referred to later below.

A blade 34 is illustrated in FIGS. 3 and 4 and FIGS. 7 and 8, respectively. In the preferred embodiment, it consists of two parallel blade legs 36, 38 which are integral with an annularly cylindrical portion 37. Blade legs 36, 38 are of a square cross-section and are dimensioned so as to be accommodated by grooves 22, 24 in an approximately matching way, the outer surfaces of blade legs 38, 38 then being located approximately at the level of the outer surface of shank 12. The outer surfaces of blade legs 36, 38 preferably may be rounded correspondingly towards the radius of shank 12, but this is not required.

The annularly cylindrical portion 37 has an outer diameter which approximately corresponds to the outer diameter of shank 12 of screw 10. In addition, it has a female-threaded portion 40 into which a threaded portion of a drive-in instrument (not shown) may be screwed. At the end opposed to the legs 36, 38, the annularly cylindrical portion 37 has two diametrical cutouts 42. These are designed to be engaged by corresponding protrusions of the drive-in instrument to prevent rotation between the drive-in instrument and the blade 34.

Figure 9:
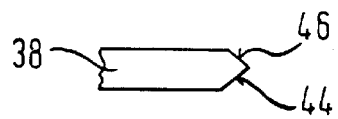
FIG. 9 shows the enlarged detail of the blade end of FIG. 4.

As can be seen particularly from FIG. 9 in which the front end of blade 34 is illustrated, blades 36, 38 have a first chamfer 44 at the end of the outer surface and a chamfer 46 at the inner surface, which form a pointed end. Chamfer 46 interacts with chamfer 28 at the bottom grooves 22, 24 to facilitate the insertion of the fork-like blade. This purpose is also served by the chamfers 26 in the groove walls, the triangularly expanded portions 48 engaging the space formed between two chamfers 26 when blade legs 36, 38 are completely inserted into grooves 22, 24. Here, the front side of the annularly cylindrical portion 37 which faces the blades bears against the distal end of screw 10. The pointed ends of blade legs 36, 38 project slightly beyond the proximal end of neck screw 10.

Figure 2:
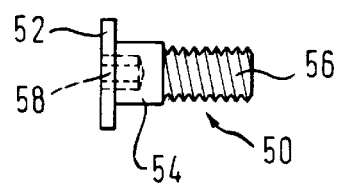
FIG. 2 shows a screw which is adapted to be screwed into the distal end of the screw of FIG. 1.
Figure 3:
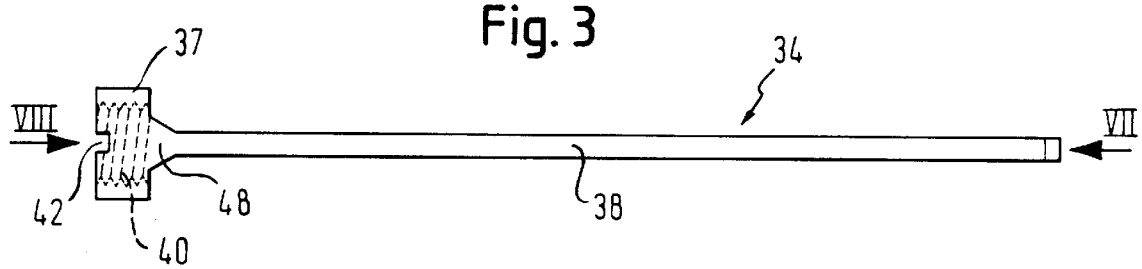
FIG. 3 shows a first side view of a blade for connection with the screw of FIG. 1.
Figure 4:
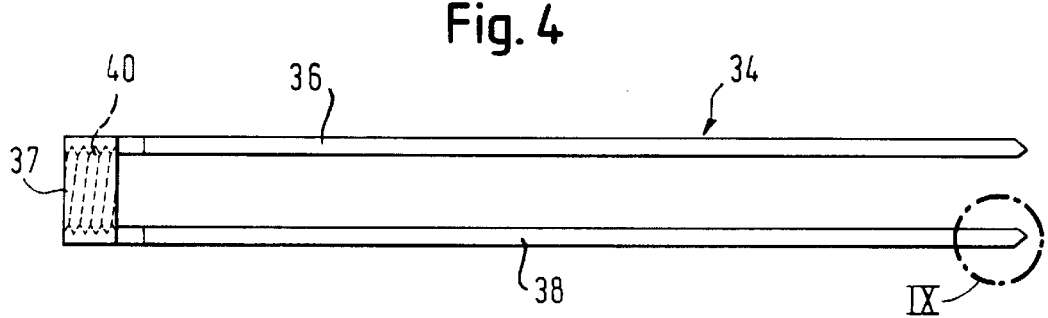
FIG. 4 shows the side view of the blade of FIG. 3 as turned by 90°.

A fastening screw 50 as shown in FIG. 2 serves to fasten the annularly cylindrical portion 37 to the distal end of screw 10. Fastening screw 50 has a disk-like head 52 of a diameter which approximately corresponds to the outer diameter of shank 12. It is followed by a smooth portion 54 to the diameter of which approximately corresponds to the major diameter of thread of the female-threaded portion 40 of the annularly cylindrical portion. A threaded portion 56 interacts with the female thread 18 of shank 12.

For an implantation, screw 10 is passed, for example, through the inclined through bore of a locking nail after an appropriate hole is drilled in the femur. Further, a preliminary hole is drilled in the neck and head of the femur. The neck screw is then screwed into the neck or head of the femur as is know per sé. A fixing or set screw (not shown) which is mounted at the proximal end of the nail shank (see U.S. Pat. No. 5,176,681), is adapted to interact with one of grooves 30, 32 to prevent another rotation after the screw 10 is turned in. In order to secure the axial position of screw 10 as well the fixing screw may be tightened so as to non-positively interact with one of grooves 30, 32 and, thus, provide an axial safety for screw 10, too. Neck screw 10 is screwed in by means of a pointed guide wire (not shown), which was driven in before and which has screw 10 "lined up" on itself, the pointed guide wire extending through the central bore 20.

Subsequently, the blade illustrated in FIGS. 1 to 3 and 4 and 7 and 8, respectively, is driven in, namely by means of an instrument which interacts with threaded portion 40.

Blade legs 36, 38 are inserted into grooves 22, 24 and are propelled until the annularly cylindrical portion 37 abuts the distal end of screw 10. After this, blade 34 is fixed to shank 12 of screw 10 by means of screw 50. For actuation, screw 50 has a countersunk drive portion 58 any well known drive surfaces (such as an Allen type).

Once blade 34 is fixed as described the fixing screw may be slightly loosened with respect to one of grooves 30, 32 in a way that screw 10, although being secured from rotation as before, may slide in an axial direction to allow compression of a neck or head fracture.

We claim:

1. A neck screw for a medullary nail comprising a shank having an outer surface, a threaded portion at a proximal end and a tool engagement surface at a distal end, a pair of axially extending grooves formed in said shank and open to said outer surface, said grooves extend on opposite sides of said shank from the distal end to the proximal end, at least one of said grooves extends into said threaded portion, and a blade having a connecting portion having a pair of legs extending therefrom for slidably engaging said grooves, the connecting portion of said blade is adapted to be connected to the distal end of the screw shank wherein said connecting portion is an annular cylindrical portion and said pair of legs are integral with the annular cylindrical portion, an outer surface of the connecting portion generally corresponds in size to the outer surface of said screw shank and a fastener is provided for fastening the annular cylindrical portion to the distal end of said shank.

2. The neck screw according to claim 1, wherein said two grooves and said legs extend into said threaded portion.

3. The neck screw according to claim 2, wherein said legs extend beyond the proximal end of said screw shank.

4. The neck screw according to claim 1, wherein said grooves extend into said shank and said legs are dimensioned in the area of the shank in such a way that outer surfaces of said legs are located approximately at the level of the outer surface of the shank.

5. The neck screw according to claim 4, wherein said grooves have deeper portions and have portions which are of a shallower depth in the area of said threaded portion and have a ramp portion between the groove portions of different depth.

6. The neck screw according to claim 1, wherein said annular cylindrical portion has a female thread for mounting to a drive-in instrument.

7. The neck screw according to claim 1, wherein the ends of said legs have a chamfer on an outer surface thereof.

8. The neck screw according to claim 1, wherein the ends of said legs have a chamfer on an inner surface thereof.

9. The neck screw according to claim 1, wherein the grooves have walls extending inwardly from an open outer surface thereof into said shank and at the distal end of the shank have a chamfer.

10. The neck screw according to claim 1, wherein the grooves have a bottom surface having a chamfer at the distal end.

11. The hip screw assembly according to claim 1 wherein said fastener is a screw.

12. A hip screw assembly comprising:
a shank having a longitudinal axis, a first end and a threaded portion at a second end, a pair of circumferentially spaced axially extending grooves formed in an outer surface of said shank and at least one groove extending from said first end towards said second end and into said threaded portion; and a blade having a pair of legs connected by a connecting portion slidably received within said grooves and at least one leg extending into said threaded portion, each of said pair of legs positioned for sliding engagement with one of said pair of grooves, said connecting portion including means for coupling said connecting portion to the first end of said shank.

13. A hip screw assembly according to claim 12, wherein said shank is cylindrical and an outer diameter of said threaded portion is generally equal to a diameter of said cylindrical shank.

14. A hip screw assembly according to claim 12, wherein said at least one groove extends inwardly from said outer surface a depth substantially equal to a thickness of said blade.

15. A hip screw assembly according to claim 12, wherein said blade extends outwardly in said at least one groove towards said outer surface in said threaded portion, a distance greater than a root diameter of said thread.

16. A hip screw assembly according to claim 12, wherein said pair of grooves are formed on opposite sides of said shank.

17. A hip screw assembly according to claim 12, wherein the connecting portion is cylindrical and has a threaded bore.

18. A hip screw assembly according to claim 12, wherein said at least one groove has a first depth in said threaded portion, less than a second groove depth at the first end of said shank.

19. A hip screw assembly according to claim 18, wherein a ramp portion extends between said first and second groove depths.

20. The hip screw assembly according to claim 12 wherein said means for coupling is a screw.

21. A hip screw assembly method comprising:
inserting a neck screw into a head region of a femur, said neck screw comprising a shank having a distal end and an outer surface with a threaded portion at a proximal end thereof, a pair of axially extending grooves open to said outer surface extending from the distal end to the proximal end of said shank and at least one groove extending into said threaded portion, said grooves circumferentially spaced on said shank;

inserting legs of a blade having a pair of legs connected by a connecting portion into a respective one of said grooves, said connecting portion engageable with a distal end of said shank; and coupling the connecting portion of said blade to the distal end of the shank with a fastener.

* * * * *

UNITED STATES PATENT AND TRADEMARK OFFICE
CERTIFICATE OF CORRECTION

PATENT NO. : 6,423,066 B1
DATED : July 23, 2002
INVENTOR(S) : Hans E. Harder and Bernhard Karich It is certified that error appears in the above-identified patent and that said Letters Patent is hereby corrected as shown below:

<u>Title page,</u>
Item [57], ABSTRACT,
Line 7, "are" should read -- and --.

<u>Column 2,</u>
Line 21, "position" should read -- positioned --.
Line 42, "effect" should read -- effected --.

<u>Column 3,</u>
Line 59, "38" (first occurrence) should read -- 36 --.

<u>Column 4,</u>
Line 55, after "58" insert -- for use with --.
Line 67, "extend" should read -- extending --.

<u>Column 5,</u>
Line 2, "extend" should read -- extending --.

Signed and Sealed this

Twenty-first Day of January, 2003

JAMES E. ROGAN
*Director of the United States Patent and Trademark Office*